US008758833B2

(12) United States Patent
Garnier et al.

(10) Patent No.: US 8,758,833 B2
(45) Date of Patent: **\*Jun. 24, 2014**

(54) **COSMETIC COMPOSITION FOR THE TREATMENT OF ACNE COMPRISING A PEPTIDE EXTRACT OF *SCHISANDRA***

(75) Inventors: Sebastien Garnier, Pierres (FR); Dalale Naaimi, Epernon (FR); Caroline Baudouin, Rambouillet (FR)

(73) Assignee: Laboratoires Expanscience, Courbevoie (FR)

( \* ) Notice: Subject to any disclaimer, the term of this patent is extended or adjusted under 35 U.S.C. 154(b) by 319 days.

This patent is subject to a terminal disclaimer.

(21) Appl. No.: 13/387,518

(22) PCT Filed: Jul. 27, 2010

(86) PCT No.: PCT/EP2010/060876
§ 371 (c)(1),
(2), (4) Date: Jan. 27, 2012

(87) PCT Pub. No.: WO2011/012615
PCT Pub. Date: Feb. 3, 2011

(65) Prior Publication Data
US 2012/0121725 A1    May 17, 2012

(30) Foreign Application Priority Data
Jul. 30, 2009    (FR) .................................... 09 55343

(51) Int. Cl.
*A61K 36/79*    (2006.01)
*A61K 38/00*    (2006.01)

(52) U.S. Cl.
USPC ............................ 424/725; 424/777; 514/1.1

(58) Field of Classification Search
None
See application file for complete search history.

(56) References Cited

U.S. PATENT DOCUMENTS

2003/0026854 A1    2/2003    Zhao

FOREIGN PATENT DOCUMENTS

| CN | 101040971 | 9/2007 |
|---|---|---|
| FR | 2822821 | 10/2002 |
| FR | 2857596 | 1/2005 |
| FR | 2910815 | 7/2008 |
| KR | 2002-0001931 | 1/2002 |
| WO | WO 98/47479 | 10/1998 |
| WO | WO 01/21150 | 5/2001 |
| WO | WO 01/21605 | 5/2001 |
| WO | WO 01/51596 | 7/2001 |
| WO | WO 2004/012496 | 2/2004 |
| WO | WO 2004/012752 | 2/2004 |
| WO | WO 2004/016106 | 2/2004 |
| WO | WO 2004/050052 | 7/2004 |
| WO | WO 2004/112741 | 12/2004 |
| WO | WO 2004/112742 | 12/2004 |
| WO | WO 2005/102259 | 11/2005 |
| WO | WO 2006/122454 | 11/2006 |
| WO | WO 2006/122485 | 11/2006 |
| WO | WO 2007/005760 | 1/2007 |
| WO | WO 2007/020382 | 2/2007 |
| WO | WO 2007/057439 | 5/2007 |
| WO | WO 2008/009709 | 1/2008 |
| WO | WO 2008/080974 | 7/2008 |

OTHER PUBLICATIONS

International Search Report issued in application No. PCT/EP2010/060876 on Jun. 28, 2011.
He, Xian-guo, et al., "Analysis of lignan constituents from *Schisandra chinensis* by liquid chromatography—electrospray mass spectrometry," Journal of Chromatography A, 757 (1997) pp. 81-87.
Huyke, Constance, et al., "Composition and Biological Activity of Different Extracts from *Schisandra sphenanthera* and *Schisandra chinensis*," Composition and Biological . . . Planta Med, (2007), 73, pp. 1116-1126.
Song, Lei, et al., "Compositions and Biological Activities of Essential Oils of *Kadsura longepedunculata* and *Schisandra sphenanthera*," The American Journal of Chinese Medicine, (2007), vol. 35, No. 2, pp. 353-364.
French Preliminary Search Report issued for priority application No. FR 0955343, dated May 7, 2010, (2 pages).
International Search Report issued for the PCT parent application No. PCT/EP2010/060876, dated Jun. 16, 2011, (2 pages).
Database wipi—XP002579998, accessed May 17, 2010.
Xin, et al., "Effects of *Schisandra sphenanthera* extract on the pharmacokinetics of tacrolimus in healthy volunteers", British Journal of Clinical Pharmacology, vol. 64, No. 4, (2007), pp. 469-475.
Zhu et al., "Variations of the Lignan Content of *Schisandra chinensis* (Turcz.) Baill. And *Schisandra sphenanthera* Rehd. et Wils.," Chromatographia, vol. 66, No. ½, (2007), pp. 125-128.
K2E-PAT Machine translation of KR2002-0001931 obtained from http://eng.kipris.or.kr on Mar. 27, 2012 (13 pages).

*Primary Examiner* — Michael G Hartley
*Assistant Examiner* — Nabila Ebrahim
(74) *Attorney, Agent, or Firm* — Foley & Lardner LLP

(57) ABSTRACT

The present invention relates to a cosmetic, nutraceutical or dermatological composition for treating or preventing acne, comprising a peptide and oside extract of *Schizandra* fruit and a suitable excipient. Preferably, the extract is obtained from *Schizandra sphenanthera*. The composition may also comprise at least one anti-acne agent selected from a sebum-regulating agent, an antibacterial and/or antifungal agent, a keratolytic agent and/or a keratoregulating agent, an astringent, an anti-inflammatory and/or anti-irritant, an antioxidant and/or a free-radical scavenger, a cicatrizing agent, an anti-ageing agent and a moisturizing agent. The invention also relates to a method for cosmetic treatment of acne, characterized in that a cosmetic composition according to the invention is applied to the affected areas of the skin, or in that the affected individual takes a nutraceutical composition according to the invention orally.

9 Claims, No Drawings

COSMETIC COMPOSITION FOR THE TREATMENT OF ACNE COMPRISING A PEPTIDE EXTRACT OF *SCHISANDRA*

The invention relates to a cosmetic composition for the treatment of acne comprising a *Schisandra* peptide extract and a suitable excipient.

There are in the world about 25 species belonging to the genus *Schisandra*. Approximately 16 of these are Chinese. These shrubs originate in northern China and adjacent regions in Russia and Korea.

*Schisandra* is a dioecious plant (with distinct male and female flowers). The fruit is in the form of a hanging cluster somewhat similar to that of the current bush. It has a naked peduncle in its upper part (roughly 5-10 cm) that is covered in its lower part by bright red berries which are slightly larger, more compact and firmer than currants. The spherical seed is a few millimeters in size.

Two species are officially recognized as medicinal in China, *S. chinensis* and *S. sphenanthera* (He et al., 1997). Their berries are used in traditional Chinese medicine to treat coughs, asthma, night sweats, nocturnal emissions and chronic diarrhea. They are also used as tonics and to treat chronic fatigue.

With the botanical name *Schisandra*, this plant belongs to the class Magnoliopsida and the order Magnoliales. The botanical family is that of Schisandraceae. The term *Schisandra* used alone may refer to two different plants, *Schisandra chinensis* and *Schisandra sphenanthera*. These two species have long been regarded as equivalent: they could be designated according to their origin, "northern *Schisandra*" for *Schisandra chinensis* and "southern *Schisandra*" for *Schisandra sphenanthera*.

*Schisandra chinensis* is known in Chinese as pinyin, wŭ wèi, literally "five flavor berry." *Schisandra chinensis* is a slow-growing, wild, deciduous and arborescent liana able to reach 9 to 10 meters in height.

*Schisandra sphenanthera* Rehd. et Wils. is also called schisandre à fleurs orangées (in France), southern *Schisandra* and lemon wood (in England), and hua zhong wu wei zi and nan wu wie zi (in China).

Although the fruit of *S. chinensis* has been the subject of an abundance of literature, much less work has been done on *S. sphenanthera*. Several reasons explain this discrepancy:
- a poorer reputation in terms of its use according to Chinese tradition,
- a near absence of use in the West,
- a lower proportion of total neolignans compared with *S. chinensis*.

One of the major differences between the two species relates to the nature and proportions of the neolignans contained in their respective fruits. This subfamily of chemical constituents is the great novelty of the genus *Schisandra*. Recently, an article by Huyke et al. (2007) reported a comparative study of the effects on cell proliferation of *S. chinensis* and *S. sphenanthera* extracts.

In Europe, no drug authorized by the competent authorities contains *Schisandra sphenanthera* extract. It is generally accepted that *S. sphenanthera* is medicinally inferior to *S. chinensis* and that it is useful only as an alternative source of active lignans.

Commercially, the fruit of *S. sphenanthera* is regarded as less costly than that of *S. chinensis*.

Characteristics of the Fruits

The dry fruit of *Schisandra* is comprised of approximately 20% essential oils, including 7% to 30% unsaponifiables (Huyke et al., 2007). Lignans are contained in the unsaponifiable fraction of the oils. Other active constituents include phytosterols and vitamins C and E.

*Schisandra* essential oil is rich in sesquiterpene derivatives (Song et al., 2007) such as δ-cadinene (25.6%), γ-cadinene, β-himachalene and santalol (Huyke et al., 2007). Essential oil of *S. chinensis* fruit contains more monoterpene hydrocarbons that that of *S. sphenanthera* fruit (Huyke et al., 2007).

*S. sphenanthera* fruit is characterized by its high deoxyschisandrin content. In contrast, its schisandrin and γ-schisandrin contents are very low compared with those of *S. chinensis* seed (Zhu et al., 2007).

Fruit Extracts: Forms Used

The form most used in traditional medicine is dried fruit. In addition to its traditional use in China in a dehydrated state, *Schisandra* fruit is also used in the form of extracts obtained by extraction solvents enabling entrainment of the fruit's neolignans. The solvents mentioned in the literature are ethanol, supercritical $CO_2$ ($SC$—$CO_2$; combined with a cosolvent or not) and hexane.

Several studies have attempted to compare the extractive capacities of $SC$—$CO_2$, chloroform, methanol and ethanol with regard to fruit neolignans.

According to a recent publication, extraction of *Schisandra* fruit by $CO_2$ or $CO_2$+5% ethanol, or by hexane, leads to extract compositions that are quite similar in terms of neolignans. In contrast, the use of ethanol led to poorer extraction of two neolignans, dehydroschisandrin and gomisin O, and apparently better extraction of γ-schisandrin (Huyke et al., 2007).

In addition, an extraction technique was developed by Zhu at al. which made it possible to compare the quantities of lignans contained in *Schisandra chinensis* and *Schisandra sphenanthera* extracts, respectively (Zhu et al., 2007).

PRIOR ART

Many pharmacological properties of *Schisandra* fruit extracts have been reported in the literature, such as:
- hepatic protection effects, known since the 1980s;
- anti-HIV effects;
- an anti-inflammatory and antitumor activity;
- an increase in the bioavailability of certain products when ingested at the same time (Xin H W et al., 2007).

Thus, many documents, examples of which are given below, cite pharmacological compositions that comprise, in addition to other active compounds, *Schisandra* extracts.

The application US 2003/0026854 by Mr. Zhao describes a schisandrin-based drug for treating liver diseases; the schisandrin is extracted in particular from *Schisandra chinensis* or *Schisandra sphenanthera*.

Applications WO 2006/122485 and WO 2006/1222454 by Guang Zhou Zhongyi Pharmaceutical describe compositions intended to treat diabetes, comprising mixtures of several plants including *Schisandra sphenanthera*.

Application WO 2007/020382 by Phynova describes a composition comprising the extracts of four plants including *Schisandra chinensis* or *Schisandra sphenanthera*, for the treatment of hepatic, metabolic and/or immune disorders, and more particularly intended to treat hepatitis C.

Application WO 2007/005760 describes a composition comprising compounds of the family of schisandrins, gomisins and other compounds arising from *Schisandra chinensis* and *Schisandra sphenanthera* fruit extracts to treat chemotherapy-resistant cancer cells.

An article by Huyke et al. (2007) describes and compares the effects of *S. sphenanthera* and *S. chinensis* extracts on cells in culture: the proliferation of HaCaT and A431 epidermal cells is inhibited in a dose-dependent manner by these extracts, with the nonpolar extracts being more effective than the polar extracts. The authors of the study conclude that the SC—$CO_2$ extract of *Schisandra sphenanthera* could be useful in the prevention and treatment of inflammatory and hyperproliferative diseases of the skin (Huyke et al., 2007).

The use of *Schisandra chinensis* extracts in the prevention of acne has been described in patent application KR 2001931, in compositions further comprising exfoliants selected from plant proteases such as papain and bromelain, or from microorganism proteases. These extracts, which are not clearly identified, are thus not used alone but in combination with exfoliants.

An anti-acne composition from traditional Chinese medicine has been described in application CN 11040971: it comprises 10 parts *Acorus calamus* called "shi chang pu," eight parts *Schisandra* fruit, and three other plants.

None of these documents describes a particular *Schisandra* extract, and in particular a peptide extract, or its cosmetic and dermatological effects on acne.

The Inventors have now discovered, in a surprising manner, that a composition comprising a *Schisandra* peptide extract may be used to treat or prevent acne, and in particular the inflammation related to the presence of the *P. acnes* bacterium.

Physiopathology of Acne

Acne is a chronic inflammatory disease of the pilosebaceous follicle which affects most adolescents and adults. The pathology varies in its presentation and its severity. Acne in adolescents is moderate or mild in 85% of cases. Among the 15% with severe acne, 3% to 4% of males and 0.4% of females have nodular and chronic acne. The common element of the various presentations resides in sebaceous retention, which is expressed clinically by specific elementary lesions.

The pathology appears as elementary lesions at various stages of development. They are retentional and/or inflammatory:

retentional lesions corresponding to distended pilosebaceous follicles;

closed comedones or microcysts (raised white elements of 1 mm to 3 mm in diameter);

open comedones or blackheads;

superficial inflammatory lesions (papules and pustules) and deep inflammatory lesions (nodules);

papule: raised red element of 1 mm to 5 mm in diameter, sometimes sensitive, often evolving toward a pustule (purulent);

nodule: deeper, with a diameter greater than 5 mm, able to evolve toward formation of an abscess and to rupture.

Acne lesions can leave permanent atrophic scarring, hypertrophic scarring, or generally transitory and/or pigmented erythematous macules.

Acne is an affection of the pilosebaceous follicle (very specific follicle with an atrophied hair) in which four tightly interlinked and successive factors intervene: hyperseborrhea, hyperkeratinization, proliferation of the bacteria *Propionibacterium acnes* (*P. acnes*) and inflammation.

Hyperseborrhea

Hyperseborrhea (sebaceous hypersecretion) is the initial factor in acne. It is essentially hormone-dependent, in particular under the effect of androgens. Indeed, the secretion of sebum is triggered and maintained by dihydrotestosterone (DHT) produced in sebaceous cells by 5-α-reductase type 1 from free testosterone. In acne, circulating androgens are present at normal levels and the pathology results from a particular sensitivity of the sebaceous gland to androgens, due in part to local 5-α-reductase hyperactivity.

Sebum consists of a mixture of squalene (12%), waxes (26%), cholesterol, cholesterol esters and triglycerides. Sebum of acneic skin contains a higher concentration of fatty acids and squalene oxides (pro-inflammatory) compared to subjects without acne, following triglyceride hydrolysis by the lipase secreted by *P. acnes*. At the same time, there is a deficit in linoleic acid (anti-inflammatory) in the comedones compared to the subjacent epidermal surface.

This inversion of the balance between pro-inflammatory and anti-inflammatory lipids is the source of the etiopathogenic factors of acne, namely the disorder of keratinization of the follicular epithelium which is a prelude to comedo formation. On the one hand, peroxidized squalene activates the lipid mediators of inflammation (increase in leukotriene B4 and prostaglandin E2) and the production of IL-6. On the other hand, the decrease in linoleic acid causes hyperkeratinization and makes the epidermis more permeable and more fragile, thus promoting the growth of microorganisms and the production of cytokines (notably interleukin-1α) and chemotactic substances which induce inflammation.

Hyperkeratinization and Comedogenesis

Hyperkeratinization is an abnormal multiplication of cells which line the internal wall of the pilosebaceous follicle (corneocytes). The corneocytes desquamate very quickly and cause the formation of a microcomedo. Obstruction of the pilosebaceous follicle canal takes place in the infrainfundibulum. This is due to anomalies in the proliferation, adhesion and differentiation of keratinocytes which do not detach from each other and block the lumen of the canal. Under normal circumstances, the corneocytes detach, which allows the sebum to pass freely to the pores. In the case of hyperkeratinization, the corneocytes remain attached to each other, hindering the sebum's way out. Thus, not only is sebum oversecreted but its discharge is restricted by the narrowing of the pores which end up being clogged. The flow of sebum trapped within the pilosebaceous follicle and cellular debris form hard and slightly white plugs of sebum which are called microcysts or closed comedones.

Keratinocyte hyperproliferation: Keratinocytes of the pilosebaceous follicle canal have a higher proliferation index (Ki-67 labeling) in acneic subjects compared with healthy control subjects. This increase in the proliferation index is found in lesional areas and in apparently healthy acne areas. It is notably related to the production of IL-1α, which is responsible for the characteristics of the microcomedo (hyperproliferation and abnormal differentiation).

Role of adhesion molecules: Integrins are adhesion molecules which ensure cohesion between keratinocytes. They act notably in the regulation of keratinocyte proliferation and migration. In acne, there is a modification of the expression of integrins α2, α3 and α5 by the infrainfundibulum keratinocytes of acne follicles. These modifications may also play a role in microcomedo formation.

Role of the composition of sebum: Hyperseborrhea decreases the linoleic acid concentration of sebum by dilution. This dearth of linoleic acid, as well as the increase in free fatty acids, induces an anomaly in infrainfundibulum keratinocyte differentiation which acts on microcomedo formation and also the triggering of inflammation.

Bacterial Proliferation/Inflammation

Inflammatory phenomena play a fundamental role in acne since they are responsible for the evolution of the pathology, notably in the formation of inflammatory lesions as well as the appearance of scarring.

This inflammatory process is multifactorial and the direct or indirect result of *P. acnes* proliferation. *P. acnes* is a commensal bacterium of the cutaneous flora. In normal skin, *P.*

*acnes* develop at the base of the pilosebaceous follicle and reach the epidermal surface via sebum. In acne, the abnormal accumulation of corneocytes and the excess of sebum in the follicular canal create an ideal environment for their development. *P. acnes* multiplication leads to the inflammatory process during the pathology.

*P. acnes* Mechanism of Action

*P. acnes* produce a variety of chemotactic factors, pro-inflammatory molecules and proteases which are responsible for the inflammatory phase of acne.

On the one hand, lipases produced by *P. acnes* hydrolyze sebum triglycerides into free fatty acids which are irritating and which release chemotactic substances toward granulocytes. These neutrophil granulocytes then release in perifollicular tissue lysosomal enzymes which cause the rupture of the pilosebaceous follicle wall with thorough diffusion of inflammation.

On the other hand, *P. acnes* use immediate immunity via Toll-like receptors (TLR2 and TLR4) on immune cells thus inducing sudden activation of the cell with release of inflammatory cytokines (IL-1α, TNFα, IL-6, IL-8, TGFα). Keratinocytes are also directly involved by the secretion of cytokines, in particular IL-1α, TNFα and the chemokine IL-8 after stimulation by *P. acnes*. The increase in IL-8 production is correlated with the hyperkeratinization of the follicle and is responsible for the rush of inflammatory cells toward the pilosebaceous follicle (chemoattractive capacity).

The activation of TLRs and of transcription factor NFκB by *P. acnes* also induces the release of MMPs (notably MMP-1, MMP-2, MMP-3 and MMP-9). These proteases attack connective fibers located around the perimeter of the pilosebaceous follicle and take part in the weakening and rupture of the distended follicular wall as well as the diffusion of inflammation in the dermis. They are also responsible for the formation of scarring.

In addition, among acne patients with a tendency to scarring, the inflammatory reaction is more intense and longer lasting with high angiogenesis. In this sense, vascular endothelial growth factor (VEGF) plays an active role in the triggering of these lesions by increasing the permeability of blood vessels that irrigate the skin, by attracting inflammatory/endothelial cells and by promoting angiogenesis.

Lastly, *P. acnes* act as superantigens directly activating T lymphocytes by binding to receptors without the intervention of antigen-presenting cells, which induces the activation of effector cells more rapidly and more effectively. The inflammatory reaction is thus amplified. Eventually, the extended inflammatory reaction accounts for the clinical presentation with the appearance of papules, pustules and nodules.

DESCRIPTION OF THE INVENTION

The Inventors have discovered that *Schisandra* fruit peptide extracts have cosmetic and dermatological properties that have never been described before now.

The object of the invention is a cosmetic, nutraceutical or dermatological composition intended to treat or prevent acne, comprising a *Schisandra sphenanthera* or *Schisandra chinensis* fruit peptide and sugar extract, in combination with a suitable excipient.

In a preferred embodiment of the invention, the peptide and sugar extract arises from *Schisandra sphenanthera*.

According to a preferred embodiment of the invention, the peptide and sugar extract is present in the composition in a percentage ranging between 0.01% and 15%, more preferentially between 0.1% and 5%, by weight in relation to the total weight of the composition. According to a preferred embodiment of the invention, the peptide and sugar extract consists of:

5% to 90% peptides, and
5% to 90% total sugars, wherein the percentages are expressed in relation to the total weight of the dry matter of said peptide extract.

The peptide and sugar extract according to the invention advantageously has the following specifications:

10% to 50% peptides, and
10% to 60% total sugars.

In the present application, the terms "peptide extract," "peptide and sugar extract" and "*Schisandra* peptides" have the same meaning and are used interchangeably to refer to the same fruit extract.

In particular, the peptide extract does not contain lignans, believed until now to be the active agents of the fruit.

According to a preferential embodiment of the invention, the peptide extract is advantageously obtained by a method comprising the following successive steps: starting with *Schisandra* fruit, extraction by supercritical $CO_2$ yields a crude oil and a defatted oil cake. The *Schisandra* berry oil cake, obtained after extraction of the lipids, is dispersed in water. Starch and fibers (cellulose, hemicellulose, etc.) are then hydrolyzed using a mixture of cellulases and α-amylases, and proteins are hydrolyzed by proteases. Treatment with heat denatures the enzymes at the end of the reaction. After centrifugation, the reaction medium is purified by ultrafiltration and diafiltration on a membrane with a 15 kDa cutoff in order to eliminate residual proteins (retentate). The permeate is then nanofiltered in order to eliminate mineral salts, and then the peptide extract is bleached with activated carbon and then filtered and recovered. Lastly, the product is filtered sterilely (0.2 μm) and may be freeze-dried or packaged.

TABLE 1

Example of an analytical composition of a peptide
and sugar extract of *Schisandra*, in percentages
in relation to dry matter:

| | |
|---|---|
| Peptide content | 13% |
| Alpha-aminated nitrogen content | 6.0% |
| Total sugar content | 44% |
| Distribution of peptide molecular weights (in Daltons) | |
| >3500 | 0% |
| 3500-1200 | 4% |
| 1200-300 | 23% |
| 300-130 | 18% |
| <130 | 55% |

According to the type of administration desired, the composition according to the invention comprises at least one pharmaceutically acceptable excipient, notably dermatologically acceptable. If the composition is cosmetic or dermatological, an excipient suited for external topical application is used.

The composition according to the present invention may further comprise at least one pharmaceutical adjuvant known to the person skilled in the art, selected from thickeners, preservatives, fragrances, colorants, chemical or mineral filters, moisturizing agents, thermal spring water, etc.

The composition according to the invention may further comprise at least one anti-acne compound selected from a sebum-regulating agent, an antibacterial agent, an antifungal agent, a keratolytic agent, a keratoregulating agent, an astringent, an anti-inflammatory/anti-irritant, an antioxidant/free-radical scavenger, a cicatrizing agent, an anti-aging agent and/or a moisturizing agent.

The term "sebum-regulating agent" refers, for example, to 5-α-reductase inhibitors, notably the active agent 5-α Avocuta® sold by Laboratoires Expanscience. Zinc and gluconate salts thereof, salicylate and pyroglutamic acid, also have sebum-suppressing activity. Mention may also be made of spironolactone, an anti-androgen and aldosterone antagonist, which significantly reduces the sebum secretion rate after 12 weeks of application. Other extracted molecules, for example from seeds of the pumpkin *Cucurbita pepo*, and squash seed oil, as well as palm cabbage, limit sebum production by inhibiting 5-α-reductase transcription and activity. Other sebum-regulating agents of lipid origin that act on sebum quality, such as linoleic acid, are of interest.

The terms "anti-bacterial agent" and "antifungal agent" refer to molecules that limit the growth of or destroy pathogenic microorganisms such as certain bacteria like *P. acnes* or certain fungi (*Malassezia furfur*). The most traditional are preservatives generally used in cosmetics or nutraceuticals, molecules with anti-bacterial activity (pseudo-preservatives) such as caprylic derivatives (capryloyl glycine, glyceryl caprylate, etc.), such as hexanediol and sodium levulinate, zinc and copper derivatives (gluconate and PCA), phytosphingosine and derivatives thereof, benzoyl peroxide, piroctone olamine, zinc pyrithione, selenium sulfide, econazole, ketoconazole, or local antibiotics such as erythromycin and clindamycin, etc.

The terms "keratoregulating agent" and "keratolytic agent" refer to an agent that regulates or helps the elimination of dead cells of the stratum corneum of the epidermis. The most commonly used keratoregulating/keratolytic agents include: alpha-hydroxy acids (AHAs) of fruits (citric acid, glycolic acid, malic acid, lactic acid, etc.), AHA esters, combinations of AHAs with other molecules such as the combination of malic acid and almond proteins (Keratolite®), the combination of glycolic acid or lactic acid with arginine or the combination of hydroxy acid with lipid molecules such as LHA® (lipo-hydroxy acid), amphoteric hydroxy acid complexes (AHCare), willow bark (*Salix alba* bark extract), azelaic acid and salts and esters thereof, salicylic acid and derivatives thereof such as capryloyl salicylic acid or in combination with other molecules such as the combination of salicylic acid and polysaccharide (beta-hydroxy acid, or BHA), tazarotene, adapalene, as well as molecules of the retinoid family such as tretinoin, retinaldehyde, isotretinoin and retinol.

The term "astringent" refers to an agent that helps constrict pores, the most commonly used being polyphenols, zinc derivatives and witch hazel.

The term "anti-inflammatory/anti-irritant" refers to an agent that limits the inflammatory reaction led by cytokines or arachidonic acid metabolism mediators and has soothing and anti-irritating properties. The most traditional are glycyrrhetinic acid (licorice derivative) and salts and esters thereof, alpha-bisabolol, *Ginkgo biloba, Calendula*, lipoic acid, beta-carotene, vitamin B3 (niacinamide, nicotinamide), vitamin E, vitamin C, vitamin B12, flavonoids (green tea, quercetin, etc.), lycopene or lutein, avocado sugars, avocado oleodistillate, arabinogalactan, lupin peptides, lupin total extract, quinoa peptide extract, Cycloceramide® (oxazoline derivative), anti-glycation agents such as carnosine, N-acetyl-cysteine, isoflavones such as, for example, genistein/genistin, daidzein/daidzin, spring water or thermal spring water (eau d'Avène, eau de la Roche Posay, eau de Saint Gervais, eau d'Uriage, eau de Gamarde), goji extracts (*Lycium barbarum*), plant amino acid peptides or complexes, topical dapsone, or anti-inflammatory drugs.

The term "antioxidant" refers to a molecule that decreases or prevents the oxidation of other chemical substances. The antioxidants/free-radical scavengers that may be used in combination are advantageously selected from the group comprised of thiols and phenols, licorice derivatives such as glycyrrhetinic acid and salts and esters thereof, alpha-bisabolol, *Ginkgo biloba* extract, *Calendula* extract, Cycloceramide® (oxazoline derivative), avocado peptides, trace elements such as copper, zinc and selenium, lipoic acid, vitamin B12, vitamin B3 (niacinamide, nicotinamide), vitamin C, vitamin E, coenzyme Q10, krill, glutathione, butylated hydroxytoluene (BHT), butylated hydroxyanisole (BHA), lycopene or lutein, beta-carotene, the family of polyphenols such as tannins, phenolic acids, anthocyanins, flavonoids such as, for example, extracts of green tea, of red berries, of cocoa, of grapes, of *Passiflora incarnata* or of Citrus, or isoflavones such as, for example, genistein/genistin and daidzein/daidzin. The group of antioxidants further includes anti-glycation agents such as carnosine or certain peptides, N-acetyl-cysteine, as well as antioxidant or free-radical scavenging enzymes such as superoxide dismutase (SOD), catalase, glutathione peroxidase, thioredoxin reductase and agonists thereof.

The agents that cicatrize/repair the barrier function which may be used in combination are advantageously vitamin A, panthenol (vitamin B5), Avocadofurane®, avocado sugars, lupeol, maca peptide extract, quinoa peptide extract, arabinogalactan, zinc oxide, magnesium, silicon, madecassic or asiatic acid, dextran sulfate, coenzyme Q10, glucosamine and derivatives thereof, chondroitin sulfate and on the whole glycosaminoglycans (GAGs), dextran sulfate, ceramides, cholesterol, squalane, phospholipids, fermented or unfermented soya peptides, plant peptides, marine, plant or biotechnological polysaccharides such as algae extracts or fern extracts, trace elements, extracts of tannin-rich plants such as tannins derived from gallic acid called gallic or hydrolysable tannins, initially found in oak gall, and catechin tannins resulting from the polymerization of flavan units whose model is provided by the catechu (*Acacia catechu*). The trace elements that may be used are advantageously selected from the group comprised of copper, magnesium, manganese, chromium, selenium, silicon, zinc and mixtures thereof.

The anti-aging agents that can act in combination to treat acne in mature subjects are antioxidants and in particular vitamin C, vitamin A, retinol, retinal, hyaluronic acid of any molecular weight, Avocadofurane®, lupin peptides and maca peptide extract.

The most commonly used moisturizers/emollients are glycerin or derivatives thereof, urea, pyrrolidone carboxylic acid and derivatives thereof, hyaluronic acid of any molecular weight, glycosaminoglycans and any other polysaccharides of marine, plant or biotechnological origin such as, for example, xanthan gum, Fucogel®, certain fatty acids such as lauric acid, myristic acid, monounsaturated and polyunsaturated omega-3, -6, -7 and -9 fatty acids (linoleic acid, palmitoleic acid, etc.), sunflower oleodistillate, avocado peptides and cupuaçu butter.

A particularly advantageous combination according to the invention is a composition comprising the *Schisandra sphenanthera* fruit peptide and sugar extract and plant and animal unsaponifiables such as, for example, avocado and soya unsaponifiables, and unsaponifiable plant or animal oil concentrates such as, for example, sunflower or palm oil concentrates, or plant oils containing unsaponifiables such as, for example, soya and rapeseed oils, and derivatives of unsaponifiables such as avocado furans, sterol esters and vitamin derivatives.

A particularly advantageous combination according to the invention is a composition comprising the *Schisandra sphenanthera* fruit peptide and sugar extract and avocado sugars (see application WO 2005/115421). Said composition is particularly suited for the treatment of cutaneous barrier repair and inflammation.

A particularly advantageous combination according to the invention is a composition comprising the *Schisandra sphenanthera* fruit peptide and sugar extract and avocado peptides (see international application WO 2005/105123). Said composition is particularly suited for the treatment of irritation and inflammation.

Another particularly advantageous combination according to the invention is a composition comprising the *Schisandra sphenanthera* fruit peptide and sugar extract and avocado oil (see international applications WO 2004/012496, WO 2004/012752, WO 2004/016106, WO 2007/057439).

Another particularly advantageous combination according to the invention is a composition comprising the *Schisandra sphenanthera* fruit peptide and sugar extract and Avocadofurane® (avocado furans, which may be obtained by the method described in international application WO 01/21605). Said composition is particularly suited for the treatment of inflammation, to promote cicatrization, and for its anti-aging properties.

Another particularly advantageous combination according to the invention is a composition comprising the *Schisandra sphenanthera* fruit peptide and sugar extract and avocado and soya unsaponifiables. The avocado and soya unsaponifiables which may be used in combination are advantageously a mixture of avocado furanic unsaponifiables and soya unsaponifiables, in a ratio of roughly 1:3-2:3, respectively. The avocado and soya unsaponifiables are even more advantageously the product Piascledine®, sold by Laboratoires Expanscience.

Another particularly advantageous combination according to the invention is a composition comprising the *Schisandra sphenanthera* fruit peptide and sugar extract and a sunflower oleodistillate, even more advantageously with a sunflower oleodistillate primarily comprising linoleic acid, such as the active agent sold by Laboratoires Expanscience, Soline® (see international application WO 01/21150). Said composition is particularly suited for the treatment of inflammation and cutaneous barrier repair.

Another particularly advantageous combination according to the invention is a composition comprising the *Schisandra sphenanthera* fruit peptide and sugar extract and a soya unsaponifiable, such as obtained according to the method described in international application WO 01/51596.

Another particularly advantageous combination according to the invention is a composition comprising the *Schisandra sphenanthera* fruit peptide and sugar extract and lupeol (FR 2822821, FR 2857596). Said composition is particularly suited to support cicatrization.

Another particularly advantageous combination according to the invention is a composition comprising the *Schisandra sphenanthera* fruit peptide and sugar extract and lupin peptides such as obtained according to the method described in application WO 2005/102259. Said composition is particularly suited for the treatment of inflammation and is used for its anti-aging properties.

Another particularly advantageous combination according to the invention is a composition comprising the *Schisandra sphenanthera* fruit peptide and sugar extract and a total lupin extract (see international application WO 2005/102259). Said composition is particularly suited for the treatment of irritation.

Another particularly advantageous combination according to the invention is a composition comprising the *Schisandra sphenanthera* fruit peptide and sugar extract and lupin oil, advantageously sweet white lupin oil, such as that described in international application WO 98/47479.

Another particularly advantageous combination according to the invention is a composition comprising the *Schisandra sphenanthera* fruit peptide and sugar extract and a maca peptide extract (see international application WO 2004/112742). Said composition is particularly appreciated for its cicatrizing and anti-aging properties.

A particularly advantageous combination according to the invention is a composition comprising the *Schisandra sphenanthera* fruit peptide and sugar extract and rice peptides (see international application WO 2008/009709). Said composition is particularly appreciated for its properties related to stimulation of melanogenesis and to melanin transfer.

Another particularly advantageous combination according to the invention is a composition comprising the *Schisandra sphenanthera* fruit peptide and sugar extract and Cycloceramide® (oxazoline derivative) such as described in international applications WO 2004/050052, WO 2004/050079 and WO 2004/112741. Said composition is particularly suited for the treatment of inflammatory reactions.

Another particularly advantageous combination according to the invention is a composition comprising the *Schisandra sphenanthera* fruit peptide and sugar extract and a quinoa extract, in particular a peptide extract (see international application WO 2008/080974). Said composition is particularly suited for the treatment of inflammatory conditions and cutaneous barrier repair.

Another particularly advantageous combination according to the invention is a composition comprising the *Schisandra sphenanthera* fruit peptide and sugar extract and cupuaçu butter. Said composition is particularly appreciated for its moisturizing properties.

Another particularly advantageous combination according to the invention is a composition comprising the *Schisandra sphenanthera* fruit peptide and sugar extract and rapeseed oleodistillate.

Another advantageous combination according to the invention is a composition comprising the *Schisandra sphenanthera* fruit peptide and sugar extract and corn oleodistillate.

All these combinations comprise at least one other active compound, in addition to the *Schisandra sphenanthera* fruit extract, and may comprise two, three, four or more active compounds as described above.

In addition to these active agents, the *Schisandra sphenanthera* fruit peptide and sugar extract according to the invention, alone or in combination with the active agents cited above, may be used in combination with sun protection active agents, such as UVB and/or UVA sun filters or screens, or any inorganic and/or organic screens or filters known to the person skilled in the art, who will adapt their choice and their concentrations according to the degree of protection sought.

As examples of sun protection active agents, particular mention may be made of titanium dioxide, zinc oxide, methylene bis-benzotriazolyl tetramethylbutylphenol (brand name: TINOSORB M) and bis-ethylhexyloxyphenol methoxyphenyl triazine (brand name: TINOSORB S), octocrylene, butyl methoxydibenzoylmethane, terephthalylidene dicamphor sulfonic acid, 4-methylbenzylidene camphor, benzophenone, ethylhexyl methoxycinnamate, ethylhexyl dimethyl PABA and diethylhexyl butamido triazone.

The composition according to the invention may be formulated in the form of various preparations suited for topical application or for oral administration.

According to a first variant, the various preparations are suited for topical application and include creams, gels, emulsions, milks, pomades, lotions, oils, aqueous or hydro-alcoholic or glycolic solutions, powders, patches, sprays or any other product for external application. Such formulations are presented in the examples below.

According to a second variant, the various preparations are suited for oral administration, wherein the *Schisandra* fruit extract may be included in a dietary supplement or in a dietary composition.

The dietary supplement may be provided in the form of hard or soft gelatin or vegetable capsules in the context of the present invention. Said dietary supplement may thus contain from 10% to 100% by weight of the *Schisandra* fruit peptide extract.

The *Schisandra* fruit peptide extracts of the present invention may also be incorporated, with no restriction, in a dietary composition such as food, a beverage and a nutraceutical, including the following:
1) Dairy products such as cheese, butter, milk and other lacteal beverages, mixtures and spreads containing lacteal products, ice cream and yogurt;
2) Fat-based products such as margarine, spreads, mayonnaise, cooking fats, frying oils and vinaigrettes;
3) Cereal-based products composed of grains such as bread and pasta, whether these food products are cooked, baked or processed.
4) Confections such as chocolate, candy, chewing gum, desserts, toppings, sorbets, icing and other garnishes;
5) Alcoholic or non-alcoholic beverages including sodas and other soft drinks, fruit juices, diet supplements, meal replacements in beverage form such as those sold under the brand names Boost™ and Ensure™, and;
6) Various products such as eggs, processed food such as soup, ready-to-use pasta sauces, prepared dishes and other products of the same type.

The *Schisandra* peptide extract may be incorporated directly and with no other modification in foods, in nutraceuticals, in diet products, in particular high-protein products, or in beverages by virtue of techniques such as mixing, infusion, injection, blending, absorption, kneading and spraying. Such formulations are presented in the examples below.

The modes of administration, dosing schedules and optimal galenic forms of the compounds and compositions according to the invention may be determined according to criteria generally taken into account in the establishment of a pharmaceutical treatment, in particular a dermatological treatment, suited to a patient such as, for example, the patient's age or weight, the gravity of the patient's general state, tolerance to the treatment, noted side effects and skin type.

The invention also relates to a method of cosmetic treatment of acne, characterized in that a cosmetic composition according to the invention is applied to the affected areas of the skin.

The invention also relates to a method of cosmetic treatment of acne by oral route, characterized in that the affected individual takes a nutraceutical composition according to the invention orally.

The present invention also relates to the use of *Schisandra* fruit peptide and sugar extract for the preparation of a cosmetic, nutraceutical or dermatological composition intended to treat or prevent acne.

In the context of a cosmetic or dermatological use, the composition will advantageously be formulated in the form of a preparation suited to topical application.

In the context of use in food, to nutritive or cosmetic ends (cosmetic foods), the composition will advantageously be formulated in the form of a preparation suited to oral administration.

In particular, said composition is intended to inhibit inflammation, via specific action on *P. acnes*. *Schisandra* peptides specifically target the inflammatory process of acne which plays a central role in the development and aggravation of the pathology. Thus, the examples presented below show that *Schisandra* peptides have several effects on keratinocytes:
An anti-inflammatory effect: inhibition of early (IL-1α, IL-1β and late (IL-8) mediators of inflammation.
An inhibitory effect on the induction of MMPs (MMP-2 and MMP-9) by keratinocytes.
An inhibitory effect on VEGF release.

*Schisandra* peptides also have an effect on the *P. acnes* bacterium:
Inhibition of IL-8 induction by *P. acnes*.
Inhibition of MMP-9 induction by *P. acnes*.

EXAMPLES

Example 1

Effects of *Schisandra* Peptide Extract on Acne Prevention and Treatment

Materials and Methods

Keratinocyte Monolayer Model: Study of IL-1α, IL-1β, IL-8, MMP-2 and MMP-9 Expression Keratinocytes were seeded in 24-well plates at a density of 120,000 cells/well. After 24 hours of incubation at 37° C. and 5% $CO_2$, the cells were treated with 0.05% and 0.1% *Schisandra* peptides in the culture medium for 48 hours.

Keratinocyte/*P. acnes* Co-Culture Model: Study of MMP-9 Expression

HaCaT cells were cultured to confluence in 24-well polystyrene plates at 37° C. and 5% $CO_2$. They were then treated with *Schisandra* peptides for 30 minutes, and then incubated or not incubated for 16 hours in the presence of *P. acnes*.

After each treatment, the culture supernatants were eliminated and total RNA extracted using an extraction kit (RNeasy Mini Kit, Qiagen). Total RNA were then assayed in chips using the Experion™ system and the Experion RNA StdSens kit (Bio-Rad) and then reverse-transcribed into cDNA using the iScript cDNA Synthesis kit (Bio-Rad).

The neo-synthesized cDNA relating to the genes of interest (IL-1α, IL-1β, IL-8, MMP-2, MMP-9) or to the reference genes were amplified selectively by real-time PCR on an iQ5 system (Bio-Rad) using SybrGreen technology (iQ SybrGreen kit, Bio-Rad).

Keratinocyte Monolayer Model: Effect on IL-1α and VEGF

Keratinocytes were seeded in 24-well plates in KGM2 medium. After 24 hours of incubation, the cells were pre-treated with *Schisandra* peptides for 24 hours. Next, the cells were stimulated by adding 10 µg/ml PMA (phorbol 12-myristate 13-acetate, Sigma) for 24 hours.

After the treatment, the cell supernatants were collected and IL-1α and VEGF were assayed using ELISA kits (R&D Systems) according to the manufacturer's instructions.

An MTT (IL-1α) or neutral red (VEGF) test was carried out on the cell layers: OD, proportional to the quantity of living cells, is read at 570 nm (MTT) or 540 nm (red neutral).

The quantities of IL-1α and VEGF are expressed in pg/ml/$OD_{570}$ and pg/ml/$OD_{540}$, respectively.

Keratinocyte/*P. acnes* Co-Culture Model: Effect on IL-8 Production

HaCaT cells were cultivated to confluence in 24-well polystyrene plates at 37° C. and 5% $CO_2$. They were then treated or not treated (positive control) with *Schisandra* peptides for 30 minutes, and then incubated for 16 hours in the presence of *P. acnes*. The quantity of IL-8 produced (in pg/ml) was measured using an ELISA kit (R&D Systems) according to the manufacturer's instructions.

Calculation Method:

The real-time RT-PCR method enables the relative quantification of the expression level of a gene of interest in relation to that of a reference gene in response to a given treatment.

The quantitative analysis of the results is based on the collection of threshold cycles. The threshold cycle (Ct) is the point at which the fluorescence emission signal is statistically and significantly higher than the background. The threshold cycle is directly correlated with the initial number of copies of target DNA.

For each sample, the expression level of the gene of interest was normalized by the expression level of the most stable reference gene. The most stable reference gene was determined using the GeNorm macro.

ΔCt is thus calculated as follows:

$$\Delta Ct = Ct_{target\ gene} - CT_{reference\ gene}$$

ΔCt values were compared in a statistical test (Student's t-test) in order to evaluate the significance of the results obtained.

In a second step, the variation, as a function of the treatment and the number of copies of the gene of interest, was determined. ΔΔCt is thus calculated as follows:

$$\Delta\Delta Ct = \Delta Ct_{control} - \Delta CT_{treated}$$

Lastly, relative quantity (RQ) is calculated: $RQ = (1+E)^{\Delta\Delta Ct}$.

E (efficiency) is considered equal to 1, and thus:

$$RQ = 2^{\Delta\Delta Ct}$$

For the study of the expression of genes of interest, the percentage of inhibition was calculated as follows:

$$\frac{100 - RQ_{treated\ cells}}{RQ_{stimulated\ cells}} \times 100$$

Statistics

The significance of the results was evaluated by a Student's t-test: \$ p<0.05; * p<0.01.

Results

A. Effect of *Schisandra* Peptides on the Primary Mediators of Inflammation: IL-1α and IL-1β

1. Analysis of the Expression of Genes Coding for IL-1α and IL-1β

After 48 hours of treatment, the 0.05% and 0.1% *Schisandra* peptides tested significantly inhibit IL-1α gene expression (−78% to −97%; table 1) and IL-1β gene expression (−80% to −90%; table 2) in keratinocytes.

TABLE 1

IL-1α gene expression in keratinocytes

| IL-1α analysis | RQ | % inhibition | p value |
|---|---|---|---|
| Control | 1 | | |
| 0.05% *Schisandra* peptides | 0.22 | −78 | p < 0.01 |
| 0.1% *Schisandra* peptides | 0.08 | −97 | p < 0.01 |

TABLE 2

IL-1β gene expression in keratinocytes

| IL-1β analysis | RQ | % inhibition | p value |
|---|---|---|---|
| Control | 1 | | |
| 0.05% *Schisandra* peptides | 0.2 | −81 | p < 0.05 |
| 0.1% *Schisandra* peptides | 0.1 | −90 | p < 0.05 |

2. Analysis of IL-1α Release

The influence of *Schisandra* peptides on IL-1α synthesis and secretion by keratinocytes was then evaluated. The results are presented in table 3.

The stimulation of keratinocytes by PMA for 24 hours induces a significant release of IL-1α (+123%). In contrast, pretreatment with $10^{-7}$ M dexamethasone (reference molecule) results in total inhibition (−100%) of the release induced by treatment with PMA. This result was expected and validates the test.

Table 3: Assay of IL-1α Released by Keratinocytes

In addition, pretreatment with *Schisandra* peptides for 24 hours inhibits the IL-1α synthesis and release induced by PMA (strong inhibition of about 30% with 0.1% PMA).

B. Effect of *Schisandra* Peptides on IL-8 Expression: Secondary Mediator of Inflammation 1. Analysis of the Expression of the Gene Coding for IL-8

After 48 hours of treatment, the 0.05% and 0.1% *Schisandra* peptides tested significantly inhibit IL-8 gene expression in keratinocytes (−73% to −86% inhibition) (table 4).

TABLE 4

IL-8 gene expression in keratinocytes

| | RQ | % inhibition | p value |
|---|---|---|---|
| Control | 1 | | |
| 0.05% *Schisandra* peptides | 0.3 | −73 | p < 0.01 |
| 0.1% *Schisandra* peptides | 0.1 | −86 | p < 0.05 |

2. Effect on IL-8 Production in Keratinocytes Stimulated by *P. acnes*

The treatment of keratinocytes with a suspension of *P. acnes* very strongly stimulates IL-8 release, a secondary marker of inflammation (table 5).

A 30-minute pretreatment with *Schisandra* peptides inhibits IL-8 release by keratinocytes. Inhibition of IL-8 production begins at 0.5% and is total at 2%.

TABLE 5

Assay of IL-8 in keratinocyte/*P. acnes* co-cultures

| | Average IL-8 (pg/ml) | % stimulation (*P. acnes* control in relation to the untreated control) | % inhibition (calculated in relation to the positive *P. acnes* control) |
|---|---|---|---|
| Non-stimulated control | 70.2 | | |
| Positive control: *P. acnes* | 804.21 | +1146 | |
| *P. acnes* + 0.5% *Schisandra* peptides | 630.95 | | −22 |
| *P. acnes* + 1% *Schisandra* peptides | 507.45 | | −37 |
| *P. acnes* + 5% *Schisandra* peptides | 3.95 | | −100 |

C. Effect of *Schisandra* Peptides on Matrix Proteases MMP-2 and MMP-9

1. Analysis of MMP-2 Expression

The treatment of keratinocytes for 48 hours with 0.05% *Schisandra* peptides results in significant inhibition of MMP-2 gene expression (−68% inhibition) (table 6).

TABLE 6

MMP-2 gene expression in keratinocytes

| | RQ | % inhibition | p value |
|---|---|---|---|
| Control | 1 | | |
| 0.05% *Schisandra* peptides | 0.318 | −68 | $p < 0.01$ |

2. Analysis of MMP-9 Expression

Among the matrix proteases involved in the pathology of acne, MMP-9 plays a particularly important role. Indeed, this protease is positively regulated by pro-inflammatory cytokines but also by *P. acnes*.

Keratinocyte Monolayer Model

As shown in table 7, the analysis of Q-PCR results demonstrates inhibition of MMP-9 gene expression in keratinocytes after 48 hours of treatment with *Schisandra* peptides (−65% at 0.05% and −57% at 0.1%).

TABLE 7

MMP-9 gene expression in keratinocytes

| | RQ | % inhibition | p value |
|---|---|---|---|
| Control | 1 | | |
| 0.05% *Schisandra* peptides | 0.349 | −65 | $p < 0.01$ |
| 0.1% *Schisandra* peptides | 0.431 | −57 | $p < 0.01$ |

Keratinocyte/*P. acnes* Co-Culture Model

Similarly, modulation of MMP-9 expression was also evaluated in the keratinocyte/*P. acnes* co-culture model (table 8).

Using this model, a stimulatory effect on MMP-9 gene expression by the *P. acnes* bacterial suspension was demonstrated (+37%).

In contrast, pretreatment of keratinocytes with *Schisandra* peptides counters this stimulatory effect by *P. acnes* and also inhibits it (−49% and −53% in relation to keratinocytes treated with the bacterial suspension).

TABLE 8

MMP-9 gene expression in keratinocyte/*P. acnes* co-cultures

| | RQ | % inhibition | p value |
|---|---|---|---|
| Untreated control | 1 | | |
| Positive control: *P. acnes* | 1.371 | | $p < 0.05$ |
| *P. acnes* + 0.5% *Schisandra* peptides | 0.69 | −49 | $p < 0.05$ |
| *P. acnes* + 1% *Schisandra* peptides | 0.739 | −53 | $p < 0.05$ |

D. Effect of *Schisandra* Peptides on Angiogenesis (VEGF)

Lastly, the potential inhibitory effect of *Schisandra* peptides on VEGF synthesis and release by keratinocytes was studied. The results are presented in table 9.

Thus, the stimulation of keratinocytes by PMA for hours induces a large and significant release of VEGF (+269%). In contrast, pretreatment of keratinocytes with *Schisandra* peptides for 24 hours counters this effect and significantly inhibits it (−39% at both concentrations).

TABLE 9

Assay of VEGF in keratinocytes

| | Average VEGF (pg/ml) | % stimulation (PMA in relation to the untreated control) | % inhibition (*Schisandra* peptides in relation to PMA) | p value |
|---|---|---|---|---|
| Non-stimulated control | 208.166 | | | |
| Positive control (PMA) | 767.941 | +369 | | $p < 0.01$ |
| 0.05% *Schisandra* peptides | 466.797 | | −39.2 | $p < 0.05$ |
| 0.1% *Schisandra* peptides | 465.736 | | −39.4 | $p < 0.01$ |

Example 2

Examples of Cosmetic Formulations

The Inventors present below several compositions for topical application, particularly indicated for acne.

The term "*Schisandra* peptides" indicates below a *Schisandra chinensis* or *Schisandra sphenanthera* peptide and sugar extract.

| Raw material/brand name | % |
|---|---|
| Cleansing cream | |
| Purified water | QSP 100% |
| Arlatone | 10%-30% |
| Cocoglucoside | 5%-20% |
| Hydroxypropyl guar | 1%-5% |
| Capryloyl glycine | 0%-2% |
| Preservatives | 0%-2% |
| Fragrance | 0%-1% |
| Citric acid | 0%-1% |
| Zinc PCA | 0%-1% |
| *Schisandra* peptides | 0.01%-5% |
| Sebum-regulating anti-acne emulsion | |
| PEG 40 stearate | 1%-5% |
| PEG 5 glyceryl stearate | 1%-5% |
| Ceresin wax | 1%-5% |

-continued

| Raw material/brand name | % |
|---|---|
| Glycerol monostearate | 1%-5% |
| Sorbitan stearate | 0%-2% |
| Cetyl alcohol | 0%-2% |
| Dimalate alcohol | 5%-20% |
| Vitamin E | 0%-1% |
| 5-α Avocuta | 1%-5% |
| *Schisandra* peptides | 0.01%-5% |
| Butylene glycol | 1%-5% |
| Piroctolamine | 0%-1% |
| Preservatives | 0%-1% |
| Glycerol | 1%-10% |
| Xanthan gum | 0%-1% |
| Zinc PCA | 0%-2% |
| Rice starch | 1%-5% |
| Nylon 6 | 0%-2% |
| Polyacrylamide gel | 1%-5% |
| Vitamin B6 | 0%-1% |
| Fragrance | 0%-1% |
| Purified water | QSP 100% |

Anti-inflammatory anti-acne emulsion

| Raw material/brand name | % |
|---|---|
| PEG 40 stearate | 1%-5% |
| PEG 5 glyceryl stearate | 1%-5% |
| Ceresin wax | 1%-5% |
| Glycerol monostearate | 1%-5% |
| Sorbitan stearate | 0%-2% |
| Cetyl alcohol | 0%-2% |
| Dimalate alcohol | 5%-20% |
| Vitamin E | 0%-1% |
| Vitamin B3 | 1%-5% |
| Maca peptide extract | 1%-5% |
| *Schisandra* peptides | 0.01%-5% |
| Butylene glycol | 1%-5% |
| Piroctolamine | 0%-1% |
| Preservatives | 0%-1% |
| Glycerol | 1%-10% |
| Xanthan gum | 0%-1% |
| Zinc PCA | 0%-2% |
| Rice starch | 1%-5% |
| Nylon 6 | 0%-2% |
| Polyacrylamide gel | 1%-5% |
| Vitamin B6 | 0%-1% |
| Fragrance | 0%-1% |
| Purified water | QSP 100% |

Repairing anti-acne emulsion

| Raw material/brand name | % |
|---|---|
| PEG 40 stearate | 1%-5% |
| PEG 5 glyceryl stearate | 1%-5% |
| Ceresin wax | 1%-5% |
| Glycerol monostearate | 1%-5% |
| Sorbitan stearate | 0%-2% |
| Cetyl alcohol | 0%-2% |
| Dimalate alcohol | 5%-20% |
| Vitamin E | 0%-1% |
| Panthenol | 0%-5% |
| Maca peptide extract | 0.1%-5% |
| *Schisandra* peptides | 0.01%-5% |
| Butylene glycol | 1%-5% |
| Piroctolamine | 0%-1% |
| Preservatives | 0%-1% |
| Glycerol | 1%-10% |
| Xanthan gum | 0%-1% |
| Zinc PCA | 0%-2% |
| Rice starch | 1%-5% |
| Nylon 6 | 0%-2% |
| Polyacrylamide gel | 1%-5% |
| Vitamin B6 | 0%-1% |
| Fragrance | 0%-1% |
| Purified water | QSP 100% |

Keratoregulating anti-acne emulsion

| Raw material/brand name | % |
|---|---|
| Isononyl isononanoate | 1%-10% |
| Isocetyl stearate | 1%-10% |
| PEG 40 stearate | 1%-5% |
| PEG 5 glyceryl stearate | 1%-5% |
| Preservatives | 0%-1% |
| C16-C18 cetyl alcohol | 0%-2% |
| PPG/SMDI polymer | 0%-1% |
| Salicylic acid | 0%-2% |
| Squalane gel | 0%-2% |
| Dioctyl ether | 1%-10% |
| Dimalate alcohol | 1%-10% |
| Sunflower extract | 1%-10% |
| Tromethamine | 1%-5% |
| Butylene glycol | 1%-10% |
| Trisodium citrate | 0%-1% |
| *Sclerotium* gum | 0%-1% |
| Rice starch | 1%-10% |
| Polyacrylamide gel | 0%-1% |
| Vitamin C | 0%-2% |
| Glycine | 0%-2% |
| Fragrance | 0%-1% |
| Vitamin E | 0%-2% |
| Citric acid | 0%-1% |
| *Schisandra* peptides | 0.01%-5% |
| Purified water | QSP 100% |

Anti-aging anti-acne emulsion

| Raw material/brand name | % |
|---|---|
| Isononyl isononanoate | 1%-10% |
| Isocetyl stearate | 1%-10% |
| PEG 40 stearate | 1%-5% |
| PEG 5 glyceryl stearate | 1%-5% |
| Preservatives | 0%-1% |
| C16-C18 cetyl alcohol | 0%-2% |
| PPG/SMDI polymer | 0%-1% |
| Salicylic acid | 0%-2% |
| Squalane get | 0%-2% |
| Dioctyl ether | 1%-10% |
| Dimalate alcohol | 1%-10% |
| Sunflower extract | 1%-10% |
| Tromethamine | 1%-5% |
| Butylene glycol | 1%-10% |
| Trisodium citrate | 0%-1% |
| *Sclerotium* gum | 0%-1% |
| Rice starch | 1%-10% |
| Polyacrylamide gel | 0%-1% |
| Vitamin C | 0%-2% |
| Glycine | 0%-2% |
| Fragrance | 0%-1% |
| Vitamin E | 0%-2% |
| Citric acid | 0%-1% |
| Retinol | 0%-5% |
| Maca peptide extract | 0.1%-5% |
| *Schisandra* peptides | 0.01%-5% |
| Purified water | QSP 100% |

Anti-bacterial anti-acne stick roll-on

| Raw material/brand name | % |
|---|---|
| Purified water | QSP 100% |
| Butylene glycol | 1%-5% |
| *Schisandra* peptides | 0.01%-5% |
| Zinc PCA | 0%-2% |
| Benzyl peroxide | 0%-2% |
| Carbomer | 0%-2% |
| Preservatives | 0%-1% |
| Citric acid | 0%-1% |
| Tromethamine | 0%-1% |

Photoprotecting anti-acne stick

| Raw material/brand name | % |
|---|---|
| Castor oil | QSP 100% |
| Oleic alcohol | 10%-20% |
| Palm oil | 10%-20% |
| Polyglycerin-3-beeswax | 10%-20% |
| Candelilla wax | 10%-20% |
| Hectorite | 10%-20% |
| Titanium dioxide | 0%-5% |
| *Schisandra* peptides | 0.01%-5% |
| Shea butter | 0%-5% |
| Vitamin E | 0%-1% |

SPF 50+ anti-acne sun cream

| Raw material/brand name | % |
|---|---|
| B4 purified water | QSP 100% |
| Titanium oxide | 10%-20% |
| Cyclopentasiloxane | 5%-15% |
| Octyl palmitate | 5%-15% |
| C12-C15 alkyl benzoate | 5%-10% |
| Decyl pentanoate | 5%-10% |

-continued

| Raw material/brand name | % |
|---|---|
| Zinc oxide | 5%-10% |
| Glycerol | 1%-5% |
| PEG-45/dodecyl glycol copolymer | 1%-5% |
| *Schisandra* peptides | 0.01%-5% |
| Sodium chloride | 1%-5% |
| Dextrin palmitate | 1%-2% |
| Vitamin E | 0%-2% |
| Preservatives | 0%-2% |
| Hydroxypropyl guar | 0%-1% |
| *Aloe vera* | 0%-1% |
| Soda lye | 0%-1% |
| EDTA 2-Na | 0%-1% |
| Zinc gluconate | 0%-1% |
| SPF 50+ anti-acne sun spray | |
| Glycerol caprylocaprate | 5%-20% |
| Cyclopentasiloxane | 10%-20% |
| Dicaprylyl carbonate | 5%-20% |
| Tinosorb S | 1%-10% |
| Titanium oxide 100 | 10%-20% |
| Hectorite | 0%-5% |
| Alpha-tocopherol | 0%-2% |
| Lauryl glucoside-glystearate | 0%-10% |
| B4 purified water | QSP 100% |
| Citric acid | 0%-2% |
| Pentylene glycol | 0%-5% |
| Glycerol | 0%-5% |
| Xanthan gum | 0%-2% |
| *Schisandra* peptides | 0.01%-5% |
| *Aloe vera* | 0%-1% |
| Zinc gluconate | 0%-1% |
| Preservatives | 0%-2% |
| Tinosorb M | 1%-10% |
| Scrub | |
| Arlatone duo | 5%-20% |
| Exfoliating agent | 1%-10% |
| *Sclerotium* gum | 1%-10% |
| Preservatives | 0%-1% |
| Capryloyl glycine | 0%-1% |
| Soda | 0%-1% |
| *Schisandra* peptides | 0.01%-5% |
| Sequestrant | 0%-1% |
| Citric acid | 0%-1% |
| Purified water | QSP 100% |
| Fragrance | 0%-1% |

The invention claimed is:

1. A cosmetic, nutraceutical or dermatological composition intended to treat acne, comprising a *Schisandra sphenanthera* fruit peptide and sugar extract and a suitable excipient, wherein the peptide and sugar extract is an in a percentage ranging between 0.01% and 15% by weight in relation to the total weight of the composition.

2. Composition according to claim 1, wherein the peptide and sugar extract is present in the composition in a percentage ranging between 0.1% and 5% by weight in relation to the total weight of the composition.

3. Composition according to claim 1, wherein the peptide and sugar extract consists of:

10% to 50% peptides, and
10% to 60% total sugars,
the percentages being expressed in relation to the total weight of said peptide extract.

4. Composition according to claim 1, wherein the peptide and sugar extract is obtained by a method comprising the following successive steps:
   starting with *Schisandra* fruit, extraction by supercritical $CO_2$ of a crude oil and recovery of a defatted oil cake;
   aqueous phase dispersion of said oil cake;
   enzymatic treatment of said oil cake with an enzymatic mixture of cellulases, proteases and alpha-amylases, then
   centrifugation, ultrafiltration, nanofiltration and
   recovery of the peptide extract.

5. Composition according to claim 1, wherein the composition further comprises at least one anti-acne agent selected from the group consisting of: a sebum-regulating agent, an antibacterial and/or antifungal agent, a keratolytic agent and/or keratoregulating agent, an astringent, an anti-inflammatory and/or anti-irritant, an antioxidant and/or free-radical scavenger, a cicatrizing agent, an anti-aging agent and a moisturizing agent.

6. Composition according to claim 5, wherein the anti-acne agent is selected from the group consisting of: pyroglutamic acid, linoleic acid, capryloyl glycine, zinc and derivatives thereof, copper, trace elements, benzoyl peroxide, ketoconazole, erythromycin, alpha-hydroxy acids of fruit and esters or derivatives thereof, salicylic acid and derivatives thereof, azelaic acid, polyphenols, glycyrrhetinic acid and esters thereof, alpha bisabolol, lupin peptides, sunflower oleodistillate, avocado sugars, avocado peptides, quinoa peptide extract, maca peptide extract, lipoic acid, beta carotene, vitamin B3 (niacinamide), lycopene, vitamin E, anthocyanins and flavonoids, isoflavones, vitamin B5 (panthenol), vitamin C, coenzyme Q10, glucosamine and derivatives thereof, glycosaminoglycans, adapalene, tazarotene, retinoids, pyrrolidone carboxylic acid, ceramides, hyaluronic acid, glycerin and urea.

7. A method for the cosmetic treatment of acne, comprising administering orally to an affected individual a nutraceutical composition according to claim 1.

8. A method for treating acne, comprising administering to the skin of a patient in need thereof of an effective amount of a cosmetic, nutraceutical or dermatological composition comprising a *Schisandra sphenanthera* fruit peptide and sugar extract and a suitable excipient, wherein the peptide and sugar extract is present in the composition in a percentage ranging between 0.01% and 15% by weight in relation to the total weight of the composition.

9. A method for treating acne, according to claim 8, wherein the composition inhibits inflammation via specific action on *Propionibacterium acnes* (*P. acnes*).

* * * * *